United States Patent [19]

Newton

[11] 4,232,663
[45] Nov. 11, 1980

[54] CERVICAL SUPPORT COLLAR

[76] Inventor: John E. Newton, P.O. Box 892, Burgaw, N.C. 28425

[21] Appl. No.: 968,796

[22] Filed: Dec. 12, 1978

[51] Int. Cl.³ ............................................. A61H 1/02
[52] U.S. Cl. .............................. 128/75; 128/DIG. 23
[58] Field of Search .................. 128/75, 78, 69, 87 B, 128/163, 164, DIG. 15, DIG. 23

[56] References Cited

U.S. PATENT DOCUMENTS

| | | | |
|---|---|---|---|
| D. 203,018 | 11/1965 | Helferich | D83/1 |
| 2,528,370 | 10/1950 | Johnston | 128/164 |
| 2,806,471 | 9/1957 | Breese | 128/DIG. 23 |
| 3,085,357 | 4/1963 | Nissen et al. | 128/DIG. 15 |
| 3,164,151 | 1/1965 | Nicoll | 128/75 |
| 3,343,532 | 9/1967 | Zumaglini | 128/75 |
| 3,374,785 | 3/1968 | Gaylord, Jr. | 128/75 |
| 3,383,708 | 5/1968 | Pappas | 128/DIG. 15 |
| 3,568,670 | 1/1969 | Gaylord, Jr. | 128/78 |
| 3,696,810 | 10/1972 | Gaylord, Jr. | 128/75 |
| 3,804,087 | 4/1974 | Sarnoff | 128/163 |
| 3,810,466 | 5/1974 | Rogers | 128/75 |
| 3,850,164 | 11/1974 | Hare | 128/75 |
| 3,964,474 | 6/1976 | Fox | 128/87 B |

Primary Examiner—Robert W. Michell
Assistant Examiner—Arthur S. Rose
Attorney, Agent, or Firm—Shlesinger, Arkwright, Garvey and Dinsmore

[57] ABSTRACT

A cervical collar which is made of a pad of resilient foam material with a scalloped depressed area at the middle of the inside surface of the collar whereby a user's chin is supported in the depression and pressure on a user's throat area is relieved by the reduced thickness provided by the depression.

5 Claims, 9 Drawing Figures

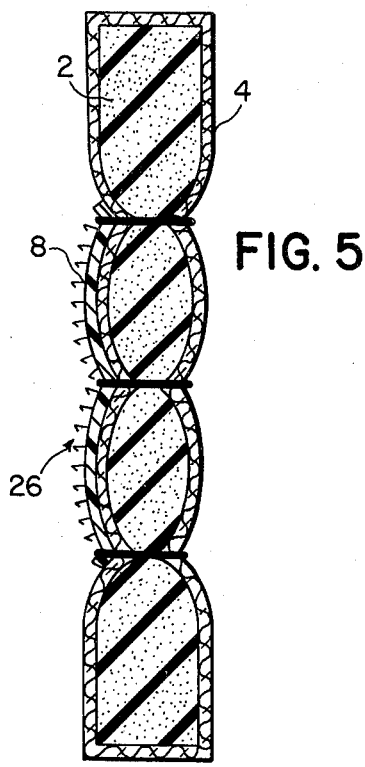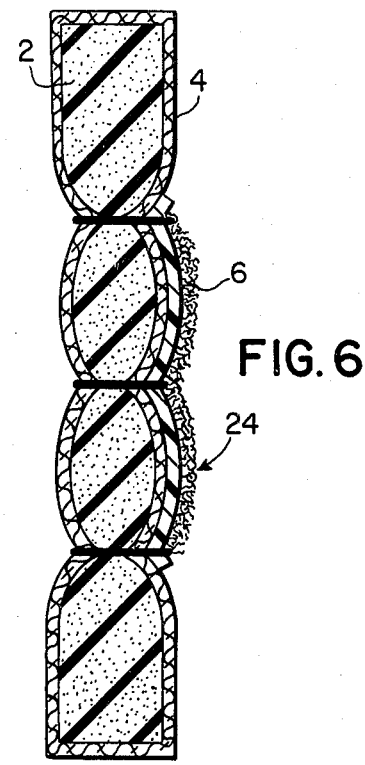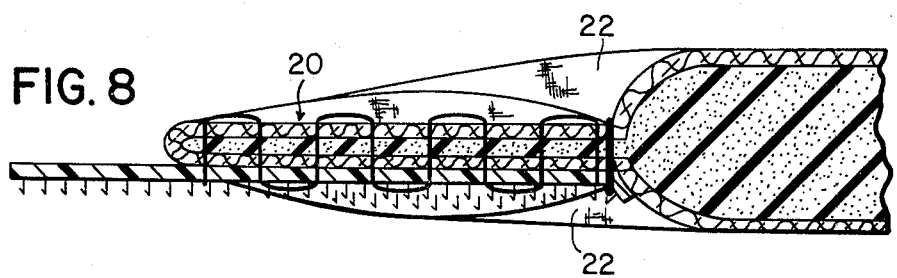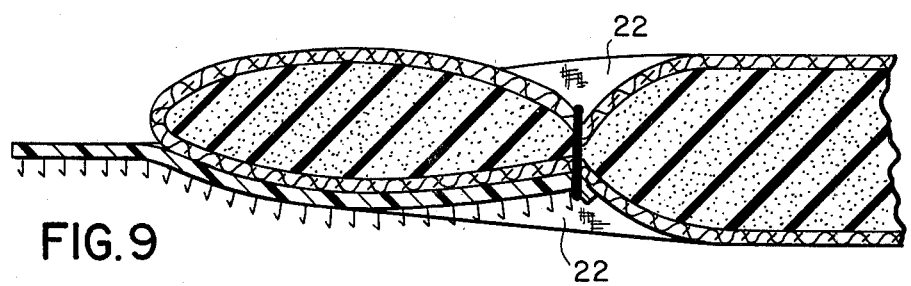

CERVICAL SUPPORT COLLAR

BACKGROUND AND FIELD OF INVENTION

This invention relates to cervical collars to be worn by persons with neck or spinal injuries in order to restrict head movement and to generally provide neck and head support to the user.

Numerous kinds of cervical collars have been used in the past to restrict the head and neck movement of a patient so as to prevent further aggravation of a neck or spinal injury. Previous collars have generally consisted of pads of foam material or the like with cut-out portions for chin support and some have contained soft foam inserts for fitting about the throat area of a user. Examples of such devices include U.S. Pat. Nos. 3,850,164 to Hare, 3,964,474 to Fox, 3,810,466 to Rogers, 3,164,151 to Nicoll and 103,018 to Helferich. None of the prior art devices however, provide a cervical collar which both adequately provides neck and head support and is comfortable when worn about the neck of a patient.

OBJECTS AND SUMMARY

It is therefore one object of the present invention to provide a cervical collar which is comprised of a resilient foam material and which, when placed around the neck of a user, easily conforms to the shape of the neck to thereby provide a comfortable fit.

It is another object of the present invention to provide a cervical collar which contains a depressed area for comfortably providing chin support and for relieving pressure on the throat area of the user.

It is another object of the present invention to provide a cervical collar wherein the resilient foam material of the collar is shape responsive to the heat and pressure generated by contact with the user and is thereby formable to the shape of the user's neck and head area.

It is a further object of the present invention to provide a cervical collar which has two bevelled ends which when fastened together provide a thickness which is substantially equal to that of the remainder of the collar and thereby produces a more comfortable fit.

It is a still further object of the present invention to provide a cervical collar which is provided with Velcro tabs at each end for easy and quick attachment of the collar.

It is another object of the present invention to provide a cervical collar which is provided with Velcro tabs which extend beyond the length of the resilient foam material thereby providing a collar which is easily variable in length.

It is a still further object of the present invention to provide a cervical collar which contains Velcro tabs which are sewn onto the collar in such a manner as to result in the tab areas having a substantially cylindrical shape in cross section; thereby, providing additional flexibility to the tab areas of the collar.

These and further objects of the present invention are accomplished by providing a cervical collar which is made of a pad of resilient foam material with a scalloped depressed area at the middle of the inside surface of the collar; whereby, a user's chin is supported in the depression and pressure on a user's throat area is relieved by the depression.

DESCRIPTION OF THE DRAWINGS

FIG. 5 is a cross sectional view taken on line 5—5 of FIG. 1.
FIG. 6 is a cross sectional view taken on line 6—6 of FIG. 1.
FIG. 8 is a cross sectional view taken on line 8—8 of FIG. 1.
FIG. 9 is a cross sectional view taken on line 9—9 of FIG. 1.

DETAILED DESCRIPTION OF THE INVENTION

Figure 3:
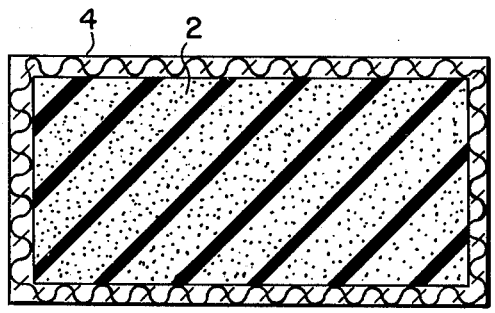
FIG. 3 is a cross sectional view taken on line 3—3 of FIG. 2.

Referring now to the drawings, the cervical collar C is generally comprised of an elongated pad of resilient foam material 2 covered with a soft knit material 4 provided with Velcro tabs 6 and 8 attached at the two ends of the pad 2 and containing depressed area 10 substantially in the middle of the inner surface of the pad 2. As shown in FIG. 3, the soft knit material 4 is used as a covering material to completely cover the foam material 2 to provide a cervical collar with improved looks and comfort about the neck of the user.

Because of its resilient characteristics, the foam material 2 used in the present invention is particularly suitable for cervical collars and the like. The particular foam material 2 used is one that cmpresses and deforms when it is subjected to heat and slight pressure but resiliently returns to its original shape after dissipation of the heat and pressure. Thus, when placed around the neck of a user, the collar will deform slightly to best comfortably fit the anatomy of a specific patient by deforming at particular points of pressure in combination with the body heat of the patient. By deforming to the particular anatomy of the patient, the collar C provides a more comfortable support collar than any other prior art devices, and yet the collar C maintains its shape and support characteristics directly adjacent to pressure points. Therefore, the collar C provides superior support for the neck and head area while also providing improved comfort.

Figure 4:
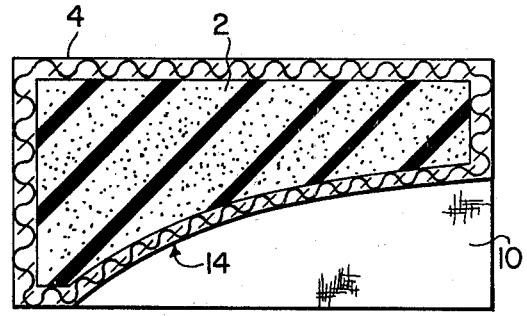
FIG. 4 is a cross sectional view taken on line 4—4 of FIG. 2.

The depressed area 10 is a concave depressed area formed in approximately the middle of the collar C and is placed in the inside face of the collar C. The concave area is recessed into the foam material 2 as shown in FIG. 4, so that at the top edge 12 of the collar C, midway of depressed area 10, the collar C is approximately ½ the thickness of areas outside of the depressed area 10. From this midway point at the top edge 12, the depth of the depression decreases and the slope 14 of depressed area 10 increases until, at the generally parabolic periphery 16 of the depressed area 10, the thickness of the collar C is the same as the areas outside of the depressed area. By reducing the thickness of the collar at the depressed area 10, the cervical collar C can tightly and securely fit about the neck of a patient without causing undue pressure on the Adam's apple and throat area. This effect is further aided by the fact that area 17, below the depressed area 10, is the same thickness as the remainder of the collar C and will therefore rest on a patient's chest and thereby aid in maintaining relieved pressure on the throat area. In addition, the chin of a patient will rest on the mid-portion of the top edge 12 at the depressed area 10 and thereby insure that the head of a patient is maintained in an upright position. In its most desirable form, the width of the depressed area 10, across the upper edge 12, is approximately between ⅛ and 1/5 of the length of the collar C.

Figure 7:
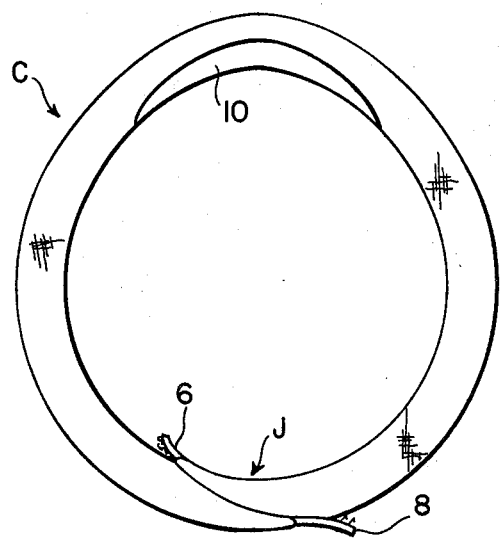
FIG. 7 is a top plan view of the cervical collar as it would be worn by a patient.

The Velcro tabs 6 and 8 attached to the ends of the collar C provide the collar with a quick and simple means of attachment about a user's neck. By extending past the collar, the Velcro tabs 6 and 8 allow for necessary length or size adjustment of the collar. The tabs 6 and 8 are preferably sewn onto the collar by stitches passing completely through the pad at the border area 18 and additionally sewn down the midline 20. This pattern of sewing attachment results, as shown in FIGS. 5 and 6, in the tab areas having a substantially cylindrical shape in cross section. This shape of the tab areas gives flexibility to the collar, in that, the collar can flex at the stitching points thus provide for a more comfortable fit and easier attachment. In addition, the particular type of sewing utilized for the Velcro tabs produces a recessed area 22 along the border area 18 on both the inner and outer faces of collar C. As shown in the cross sectional areas of FIGS. 8 and 9, this manner of stitching attaches Velcro tabs 6 and 8 so that the surfaces of the tabs are substantially level with the surface of the collar C. As a result, the joining of the two Velcro tabs 6 and 8, as shown in FIG. 7, does not create a joining area which bulges out from the remainder of the collar, but rather, is substantially the same thickness as other areas of the collar. To allow for proper attachment, the Velcro tabs are sewn on opposite sides of the collar C so that when wrapped around a user's neck, as in FIG. 7, the tabs 6 and 8 will correctly face each other for attachement. For example, tab 6 is sewn on the outside face of the collar C, with the adherent side 24 of the tab 6 facing outward, and tab 8 is sewn on the inside surface of the collar C with the barbed side 26 of tab 8 facing inward.

Figure 1:
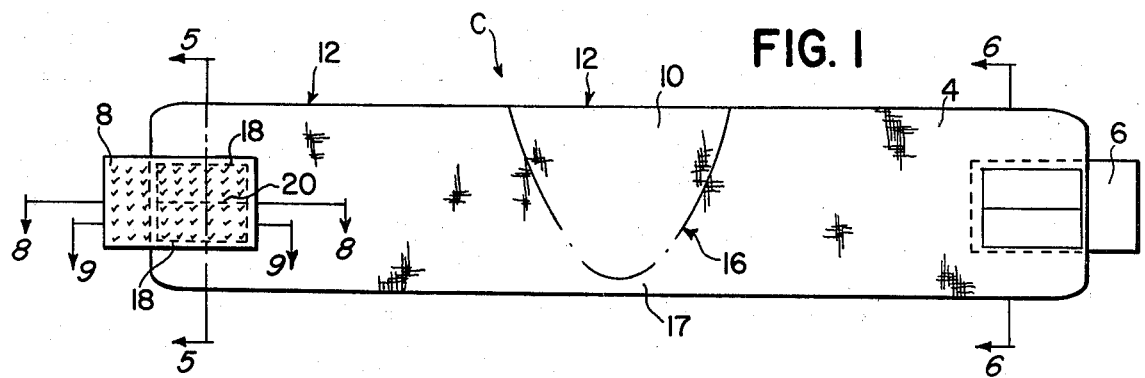
FIG. 1 is a top plan view of the cervical collar.
Figure 2:
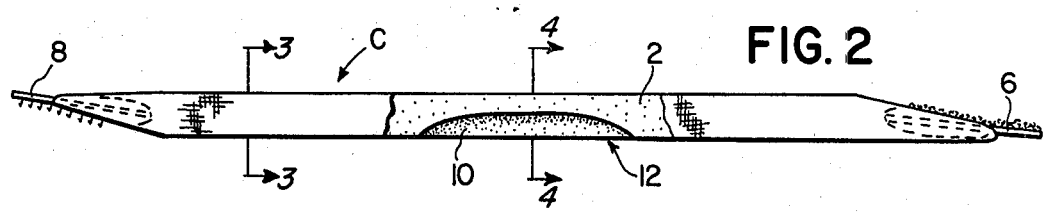
FIG. 2 is a side elevation view of the cervical collar.

The ends of the collar C are bevelled with the bevelled sides being at approximately a 30 degree angle and in the same direction, as shown in FIG. 2. When the collar is then placed about the neck of a user, the two ends of the collar overlapped and attached, the bevelling of the two ends creates a joining area J where the thickness is approximately the same as that of the remainder of the collar (see FIG. 7). This joint design substantially improves the comfort of the collar of the present invention over prior art devices, in that, with the present invention there is a total lack of annoying bulging areas at the back of the patient's neck.

While this invention has been described as having a preferred design, it will be understood that it is capable of further modification. This application, is therefore, intended to cover any variations, uses, or adaptations of the invention following the general principles thereof and including such departures from the present disclosure as come within known or customary practice in the art to which this invention pertains, and as may be applied to the essential features hereinbefore set forth and fall within the scope of this invention or the limits of the claims.

What I claim is:

1. A cervical collar for placement around a user's neck, comprising:

an elongated pad of resilient foam material generally rectangular in cross-sectional configuration having two end portions, an inner surface for placement adjacent a user's neck, an outer surface, a top edge surface and a bottom edge surface, the distance between said top and bottom edge surfaces being substantially constant along the length of said pad;

means at said end portions for detachably fastening said end portions together with said pad about the user's neck;

said pad having a depressed area in said inner surface at the longitudinal mid-portion of said pad extending from and including said top edge surface toward said bottom edge surface for the greater portion of the distance between said top and bottom edge surfaces, said depressed area being generally parabolic in outline with its apex toward said bottom edge surface; and, said inner surface within said depressed area being generally concave in form with the deepest portion of said depressed area being at said top edge surface generally at the longitudinal mid-point of said depressed area and with said depressed area decreasing in depth in either longitudinal direction from the longitudinal mid-point of said depressed area and decreasing in depth toward said bottom edge surface whereby, with the mid-portion of said top edge surface located underneath the user's chin, said depressed area acts to lessen pressure in the user's throat area.

2. The cervical collar of claim 1 wherein said resilient foam material is deformable and compressable in response to body heat and slight pressure whereby said pad will adapt in shape to the anatomy of the user.

3. The cervical collar of claim 1 wherein each said end portion is bevelled transversely of the longitudinal axis of said collar from said inner surface to said outer surface so as to have a bevelled face, said bevelled faces being parallel when said collar is at rest and cooperating when said end portions are overlapped so that the thickness of said collar between said inner and outer surfaces remains substantially constant through the area of overlap.

4. The cervical collar of claim 1 wherein at the deepest portion of said depressed area the depth of said depressed area is approximately ½ the distance between said inner and outer surfaces.

5. The cervical collar of claim 1 wherein the width of said depressed area at said top edge surface is between approximately 1/5 and ⅛ the length of said collar.

* * * * *